United States Patent

Weinhold et al.

[11] Patent Number: 5,992,224
[45] Date of Patent: Nov. 30, 1999

[54] METHOD OF DETERMINING THE DEFORMABILITY OF THE SURFACE OF A TEST SPECIMEN

[76] Inventors: Wolfgang P. Weinhold, 5 Learned Pl., Durham, N.C. 27705; Elmar Gabriel, Hofellernstr. 22, D-97209 Veitshocheim, Germany

[21] Appl. No.: 08/411,720
[22] PCT Filed: Sep. 9, 1993
[86] PCT No.: PCT/DE93/00827
   § 371 Date: Aug. 21, 1995
   § 102(e) Date: Aug. 21, 1995
[87] PCT Pub. No.: WO94/08219
   PCT Pub. Date: Apr. 14, 1994

[30] Foreign Application Priority Data

Oct. 1, 1992 [DE] Germany .............................. 42 32 982

[51] Int. Cl.$^6$ .................................................... G01N 3/48
[52] U.S. Cl. ............................................................ 73/81
[58] Field of Search .................................. 73/81–83, 789, 73/794

[56] References Cited

U.S. PATENT DOCUMENTS 4,699,000 10/1987 Lashmore et al. .......................... 73/81
5,193,383 3/1993 Burnham et al. ........................... 73/81

FOREIGN PATENT DOCUMENTS 4004344 8/1991 Germany ......................... G01N 3/46
60-091237 5/1985 Japan .

OTHER PUBLICATIONS

Patent Abstracts of Japan, vol. 9, No. 236 (P–390) (1959)21/09/95.
Mesures, vol. 57, nr. 646, Jun. 1992, Paris FR, pp. 66–67, J —P Piantino: "La durete accede au temps reel".

Primary Examiner—Robert Raevis

[57] ABSTRACT

The invention concerns a method for determining the deformability of the surface of a test specimen. Firstly, by scanning along a line on the surface with a lightly loaded stylus, the surface texture of the specimen is measured. Secondly, the same line is traversed with a loaded indenter such that the surface of the specimen is penetrated. Finally, the same line is traversed again with a lightly loaded stylus to record the new surface texture.

10 Claims, 1 Drawing Sheet

METHOD OF DETERMINING THE DEFORMABILITY OF THE SURFACE OF A TEST SPECIMEN

BRIEF SUMMARY OF THE INVENTION

The present invention relates to a computer automated and controlled method for determining the deformability of the surface of a test specimen. The invention consists of firstly scanning three times along a chosen line on the specimen's surface with a suitable stylus; once with the stylus lightly loaded giving the original surface texture, once with the stylus loaded giving the deformed surface profile and then again with the stylus lightly loaded giving the new surface texture, and secondly calculating the two differences in the resulting deformation depths between the first and third scans and between the second and third scans. The former difference gives the permanent deformation remaining after the loaded scan, the latter difference gives the elastic deformation partly recovered after the loaded scan. Knowing the stylus' scan load and geometry, the invention offers not only significant advances in continuous hardness testing but also yields information relating to the mechanical scratch and wear properties of material surfaces.

DESCRIPTION AND BACKGROUND OF THE INVENTION

Figure 1:
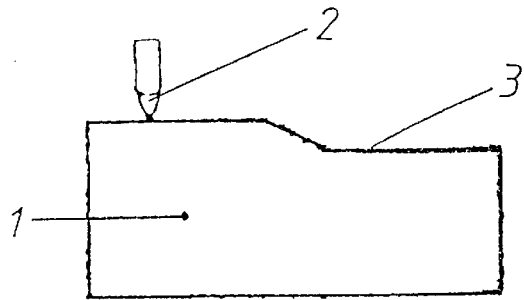
FIG. 1 illustrates the first scan, from left to right, of the test specimen's (1) surface texture (3) with the lightly loaded stylus (2).

The invention concerns a method for determining the deformability of the surface of a test specimen. Firstly, by scanning along a line on the surface with a lightly loaded stylus, the surface texture of the specimen is measured. Secondly, the same line is traversed with the now loaded stylus such that the surface of the specimen is penetrated. Finally, the same line is traversed again with the lightly loaded stylus to record the new surface texture.

Different methods are known with which the hardness and other mechanical properties, i.e. Young's modulus, near the surface of the test specimen are determined.

A closely related method is described in DE-G.M. 71 40 841: Here, the surface of the test specimen is firstly scanned with a lightly loaded stylus to record its texture. After the same line has been traversed with a loaded indenter, the surface texture is again recorded. Apart from the possible inaccuracies in the measurements, which are dependent on the different dimensions of stylus and indenter, such that the recorded surface texture does not necessarily correspond to that of the indenter's path, a further disadvantage is that it is only possible to determine the plastic component, i.e. the irreversible part of the test specimen's deformation.

In DE-OS 39 26 676 it is suggested that the stylus' indentation depth, measured as a function of applied force, is utilised for hardness testing. In addition to this, the stylus can be traversed over the test specimen's surface producing a scratch. However, since only the position of the loaded stylus is measured, this method allows only the total deformation, i.e., the sum of the elastic and plastic components of the deformation, to be recorded.

Consequently, the known methods for determining the mechanical properties of a test specimen's surface are regarded as disadvantageous, since either only the plastic component or the sum of the elastic and plastic components of the deformation can be detected. A method for measuring the elastic deformation is not known. Moreover, there is no possibility of gaining information about the form and amount of energy involved in the deformation process; for example, frictional and thermal energy.

Proceeding from the present state of the art, the problem underlying the invention is to establish a procedure for determining the deformation of a test specimen's surface that also permits a detailed investigation of both the elastic and plastic deformation and also the physical processes and form of energy involved in the deformation.

According to the invention, the problem is solved by using the stylus as the indenter, measuring the surface texture during the loaded stylus' traverse across the test specimen, displaying the difference between the final and initial measured surface textures and also the difference between the final surface texture and that recorded by the loaded stylus.

The central idea is firstly to record the test specimen's surface texture using a stylus, secondly to traverse the same path with the now loaded stylus, thirdly to record the surface texture again using the unloaded stylus and fourthly to calculate the ensuing irreversible and reversible deformations by forming the differences of the resulting surface textures. In particular, the plastic deformations correspond to the difference between the recorded surface textures before and after the scratching process. The elastic deformations equal the difference between the surface texture after the scratching process and the surface texture recorded during the scratching process. In order to maintain the smallest possible errors in measurement, the load on the stylus during the recording of the first and last surface textures should be kept sufficiently small such that no deformation of the test specimens surface, and therefore no falsification of the measured values, can take place. Since the stylus is also used to produce the scratch path, the correspondence between the subsequent recorded path of traverse and the scratch path is guaranteed. On the contrary, if the stylus were wider than the indenter, the base of the scratch path would not be detected; if the stylus were narrower than the indenter, a non-reproducible path would be traversed since the stylus would not be guided by the flanks of the scratch.

The advantages of the invention are, above all, that both the reversible and the irreversible components of the detected test piece's deformation are resolved at each position along the traversed path. The method is particularly suitable for materials having a spacially variable composition and therefore different local hardnesses, e.g. composite materials, or coated components.

If the test specimen exhibits large variations of hardness along the scratch path, the choice of load and traversing speed proves to be problematic. If both load and speed are constant, then the indentation depth for particularly hard or soft regions would be so small or large that no definitive account about the deformability of the test specimen can be given. It is therefore suggested that the stylus' load be varied during the indentation of the test specimen. Since the indentation depth at constant load and high speed is smaller than that for the same load but low traversing speed, it is alternatively or additionally possible to change the traversing speed. More specifically the speed and/or the loading force can be controlled such that a constant indentation depth results.

Apart from the resulting deformations, the corresponding expended mechanical energy is also of interest. From the local energy transformations during the deformation process, inferences about the fracture strength and the heat transfer behaviour of the test specimen can be drawn. For this reason, the measurement and recording of the force and/or power that is necessary to translate the loaded stylus along its path on the test piece is provided. A further advantage is that from the normal and tangential force, the constant of friction $\mu$ can be determined. The power that is expended in translating the stylus can, without difficulty, be determined from the electrical input to the drive unit, whilst the force can be calculated from the stylus' speed and the expended power.

Moreover, analogous to the known hardness testing procedure, it is advisable to measure and record the normal force on the stylus as a function of the indentation depth. The data enables one to analyse at each position the hardness of the test specimen perpendicular to its surface. This, for example, enables one to investigate differences between surface and subsurface regions.

Apart from the indentation depth, that is, the difference between the initial surface height and the scratch path depth, it is expedient to use the force and/or power, expended during the relative movement, as a control variable. The feedback control occurs such that the indentation depth or the force/power is held constant.

Alternatively, it is possible to vary the stylus' load and/or speed, preferably periodically, between zero and a maximum value. More specifically, the loading is composed of a static or slowly varying pre-load, and a small superimposed periodically oscillating force. From the dependency of the indentation depth on the normal force, one can obtain extensive information about the local material constitution, e.g. Young's modulus.

A disadvantage of the known procedures for determining the hardness is that no inferences concerning the local viscoelastic flow behaviour can be drawn. Since considerable differences in viscoelasticity between the matrix and the filler of composite materials frequently occur, it would be desirable in this case to have information about such material properties. It is therefore preferable that after the indentation path has been traversed by the loaded stylus, several measurements of the path are taken. From the time dependency of the geometric changes, in particular the surface texture, a detailed examination of the visoelastic behaviour can be made. By repeatedly scanning the path with the lightly loaded stylus, one can detect the time dependency of the elastic portion's recovery. In this way it is possible to establish when the recovery has terminated.

In order to gain information about the chemical composition and the properties of regions remote from the surface, it is suggested that the stylus' form and load be chosen such that the deformation is exceeded and that material is removed. The amount and chemical composition of the removed material is measured and recorded point by point and/or integrated over the total amount. Of course, the possibility exists that in order to investigate the material properties as a function of the indentation depth, the scanning of the path which removes the material is to be repeated several times. The analysis of the amount and the chemical composition of the removed materials can be carried out utilising known methods that are explained elsewhere.

Since the abrasion resistance of a test specimen is of interest, it is recommended that the deformation process under constant or varying conditions is repeated until the changes in the indentation depth or material properties are no longer evident. The number of scan cycles, which the loaded stylus makes, serves as a measure of the local abrasion or scratch resistance of the test specimen.

As an example, consider the technical application to bearings, where a layer of grease or oil is arranged between two rubbing parts. In order to be able to directly translate the measured hardness and friction values to a specific design application, it has been found to be expedient to introduce solid particles, a fluid or a suspension of solid particles in a fluid between the loaded stylus and the test specimen.

Apart from the surface texture that is detected by the loaded stylus, its immediate surroundings can be optically viewed and stored during the deformation process such that both the deformation of the material region next to the stylus and the flanks of the scratch path itself are accessible for further examination.

If the deformed region can be simultaneously observed from at least two positions, it is possible to reconstruct the three dimensional deformation process from the recorded images. Thus it is possible, for example, to analyse point by point the local material displacements.

The physical processes that accompany the deformation process are advantageously detected and recorded. In this respect for example, the emitted triboluminescence whose visible wave length can be recorded using a video camera.

Also, in order to determine the proportion of mechanical energy that is transformed into thermal energy, the heating of the test specimen and/or the stylus can be recorded point by point. Infrared detecting sensors contribute to this matter. However, the temperature can also be measured using the appropriate and sufficiently small heat sensors, e.g. thermocouples, directly on the test specimen's surface.

The acoustic and vibration phenomena detected and recorded during the deformation process can, in conjunction with the other measured values, disclose information about the local material properties and about the response of the loaded stylus.

Since the deformation process entails the emission of so-called exo-electrons, it is further suggested that a suitable sensor for their detection be installed near the test piece's surface and that the test piece itself be arranged in a vacuum chamber because of the electron's small free path.

With a view to improving the repeatability and to eliminating unknown environmental influences which falsify the measured values, the deformation process and the measuring procedure can be carried out not only in a vacuum chamber, but also under reduced air pressure, in a gas or in a vapourous atmosphere. Also the repeatability of the measured values can be suitably enhanced by maintaining a constant temperature.

In order to reduce the measuring time to its minimum, it is recommended that the prevailing surface roughness, recorded from the first scan, is utilised as the stylus' speed and/or load control variable. The advantage here is that homogenous and locally regular surface regions can be relatively rapidly scanned such that the measuring time is decisively shortened.

Finally, it is preferable to utilise a computer to both control the stylus, i.e. its traversing path, speed and loading, and also to record the measured values.

SPECIFICATION OF THE INVENTION AND DETAILED DESCRIPTION OF THE DRAWINGS

Further details, characteristics and advantages of the invention can be inferred from the following specification which, with the aid of the diagrams, illustrates the invention's form of operation.

FIG. 1 depicts the lightly loaded stylus (2) traversing, from left to right, the test specimen's (1) path (3). A step in the middle of the test specimen's (1) surface is shown.

Figure 2:
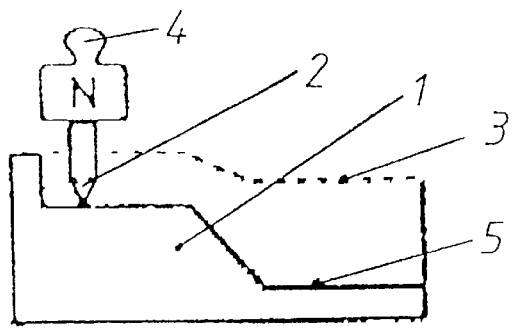
FIG. 2 illustrates the second scan, from left to right, of the test specimen (1) with a load (4) on the stylus (2) producing the deformed surface profile(5).

FIG. 2 depicts the stylus (2), which is now loaded with a weight (4), during the recording of the second surface texture (5). Due to the loading of the stylus (2), which penetrates the test specimen (1), the surface texture (5), in particular to the right of the step, is considerably lower than the initial surface texture (3). The stylus (2) is traversed from left to right.

Figure 3:
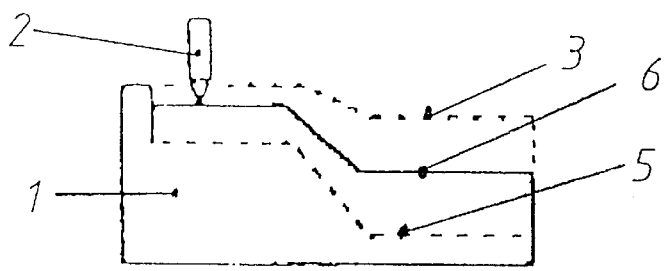
FIG. 3 illustrates the third scan, from left to right, of the test specimen (1) again with the lightly loaded stylus (2) giving the new surface profile (6) partly recovered from the deformed surface profile (5).

FIG. 3 depicts the test specimen (1) being scanned, from left to right, for a third time again with the lightly loaded stylus (2). The detected surface texture (6) is, depending on the irreversible deformation, lower than the initial surface (3) but higher than the surface (5), which resulted from the loaded stylus. Surface texture (6) results from the reversible part of the deformation causing the surface of the test piece to rise.

Figure 4:
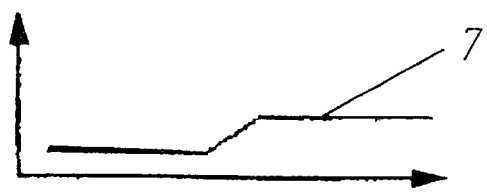
FIGS. 4 and 5 illustrate the graphic representation of the elastic (7) and permanent (8) parts of the deformation calculated by forming the differences between profiles (6) and (5) and between profiles (3) and (6) respectively.
Figure 5:
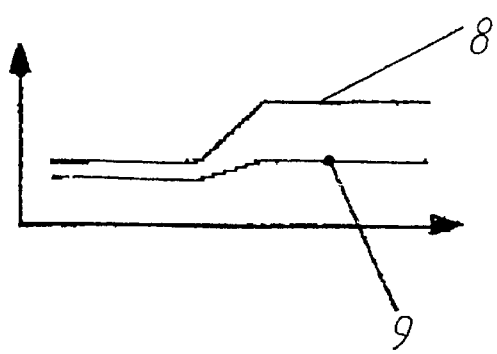

FIG. 4 depicts firstly the difference (7) between the final surface texture (6) and the surface texture (5) resulting ftom the loaded stylus is shown. This difference corresponds to the elastic or reversible deformation. Secondly, the difference (8) between the initial surface texture (3) and the final surface texture (6). This difference corresponds to the plastic or irreversible deformation.

It can be clearly seen from FIG. 4 that the test specimens (1) surface region to the right of the step is substantially softer than that to the left of the step. As a result, one obtains a procedure which enables a substantially more extensive investigation of the test specimen's deformability and of the physical processes that accompany the process of penetration.

What is claimed is:

1. A method for determining the elastic (7) and permanent (8) deformation of a test specimen's (1) surface by means of a three step measuring procedure, by which the said test specimen's (1) surface is scanned by means of an impingeing stylus (2) that both measures and loads the said specimen's (1) surface profile, together with a two step difference calculation comprising the steps of:

a) scanning along a path on the said specimen's (1) surface using the lightly loaded said stylus (2) and thereby measuring and recording the surface texture (3) from the said stylus' (1) deflection perpendicular to the said specimen's (1) surface;

b) scanning along the same said path on the said specimen's (1) surface using the now normally loaded (4) said stylus (2) which indents the said specimen's (1) surface and thereby measuring and recording the resulting deformed surface texture (5) from the said stylus' (2) deflection perpendicular to the said surface;

c) scanning again the same said path on the said specimen's (1) surface using the lightly loaded said stylus (2) and thereby measuring and recording the partly recovered surface texture (6) from the said stylus' (2) deflection perpendicular to the said specimen's (1) surface;

d) calculating and displaying the differences (7) and (8) between the above measured said surface textures (6) and (5) and between (3) and (6) respectively.

2. The method of claim 1 wherein the force and/or power necessary for translating the said loaded stylus (2) along the said path on the said specimen (1) is measured and recorded.

3. The method of claim 1 wherein the said stylus' (2) normal force is measured and recorded as a function of the said measured indentation depth.

4. The method of claim 1 wherein the said deformed surface texture (5) is scanned with the said lightly loaded stylus (2) several times.

5. The method of claim 1 wherein the said stylus (2) and its normal load are so chosen that material is removed from the said sample's (1) surface and whose amount and chemical composition is measured and recorded point by point and/or integrated over the total said scan path length.

6. The method of claim 1 wherein the said sample's (1) surface is repeatedly scanned with the said normally loaded stylus (2) until the said indentation or the material properties of the said specimen's (1) surface remains constant.

7. The method of claim 1 wherein a layer of solid particles or a fluid or a suspension of solid particles in a fluid is introduced between the said normally loaded stylus (2) and the said specimen's (1) surface.

8. The method of claim 1 wherein the said indented surface texture (5) of the said specimen (1) is optically monitored and recorded from at least two positions simultaneously so that a three dimensional reconstruction of the said indentation process results.

9. The method of claim 1 wherein the said indentation process is carried out in a controlled environment either a) under reduced air pressure, or;

b) in a vacuum, or;

c) in a gaseous atmosphere, or;

d) in a vapourous atmosphere, or;

e) at constant or varying temperature.

10. The method of claim 1 wherein a computer controls the said stylus (2), the said sample's movement and also records the measured values.

* * * * *